(12) United States Patent
Ashtekar et al.

(10) Patent No.: US 10,451,604 B2
(45) Date of Patent: Oct. 22, 2019

(54) METHODS OF MEASURING HYDROGEN SULFIDE CONCENTRATIONS IN RESERVOIR FLUIDS

(71) Applicant: SHELL OIL COMPANY, Houston, TX (US)

(72) Inventors: Sunil Ashtekar, Houston, TX (US); Richard Pollard, Pearland, TX (US)

(73) Assignee: SHELL OIL COMPANY, Houston, TX (US)

( * ) Notice: Subject to any disclaimer, the term of this patent is extended or adjusted under 35 U.S.C. 154(b) by 97 days.

(21) Appl. No.: 15/555,876

(22) PCT Filed: Mar. 4, 2016

(86) PCT No.: PCT/US2016/020933
§ 371 (c)(1),
(2) Date: Sep. 5, 2017

(87) PCT Pub. No.: WO2016/144774
PCT Pub. Date: Sep. 15, 2016

(65) Prior Publication Data
US 2018/0045705 A1    Feb. 15, 2018

Related U.S. Application Data

(60) Provisional application No. 62/129,157, filed on Mar. 6, 2015.

(51) Int. Cl.
*E21B 49/08*    (2006.01)
*G01N 31/22*    (2006.01)
*G01N 21/64*    (2006.01)
*G01N 33/28*    (2006.01)

(52) U.S. Cl.
CPC ........ *G01N 33/287* (2013.01); *E21B 49/082* (2013.01); *G01N 21/643* (2013.01); *G01N 31/22* (2013.01); *E21B 2049/085* (2013.01)

(58) Field of Classification Search
CPC ........... E21B 2049/085; E21B 49/082; G01N 21/643; G01N 31/22; G01N 33/287
See application file for complete search history.

(56) References Cited

U.S. PATENT DOCUMENTS

| | | | |
|---|---|---|---|
| 6,223,822 B1 | 5/2001 | Jones | |
| 6,469,636 B1 | 10/2002 | Baird et al. | |
| 7,128,144 B2 | 10/2006 | Fox et al. | |
| 2002/0121370 A1* | 9/2002 | Kurkjian | E21B 49/081 166/250.01 |
| 2003/0134426 A1 | 7/2003 | Jiang et al. | |
| 2006/0032301 A1 | 2/2006 | Difoggio | |
| 2006/0054501 A1 | 3/2006 | Jiang et al. | |
| 2006/0243603 A1 | 11/2006 | Jiang et al. | |

(Continued)

OTHER PUBLICATIONS

Yu et al., "Fluorescent probes for hydrogen sulfide detection and bioimaging", Chemical Communications—3hemComm, vol. 50, No. 82, Jun. 6, 2014, pp. 12234-12249, XP055268282. (Year: 2014).*

(Continued)

*Primary Examiner* — Jennifer Wecker (57) ABSTRACT

A chemical probe composition comprising a base fluid and a chemical probe, wherein the chemical probe is capable of reacting with hydrogen sulfide to form a fluorophore and associated methods and systems.

20 Claims, 3 Drawing Sheets

(56) References Cited

U.S. PATENT DOCUMENTS

| | | |
|---|---|---|
| 2009/0107667 A1 | 4/2009 | Mullins et al. |
| 2010/0050761 A1 | 3/2010 | Lawrence et al. |
| 2011/0247879 A1 | 10/2011 | Johnston et al. |
| 2012/0149117 A1 | 6/2012 | Lawrence et al. |
| 2012/0211650 A1 | 8/2012 | Jones et al. |
| 2012/0276648 A1 | 11/2012 | Van Hal et al. |
| 2013/0056626 A1 | 3/2013 | Shen et al. |
| 2013/0071934 A1 | 3/2013 | Indo et al. |

OTHER PUBLICATIONS

Duan et al., "Recent Advances in Fluorescent Probes for Monitoring of Hydrogen Sulfide", Current Medicinal Chemistry, vol. 20, No. 23, Aug. 1, 2013, pp. 2929-2937, XP055268237. (Year: 2013).*

International Search Report and Written Opinion received for PCT Patent Application No. PCT/US2016/020933, dated May 3, 2016, 10 pages.

Duan et al., "Recent Advances in Fluorescent Probes for Monitoring of Hydrogen Sulfide", Current Medicinal Chemistry, vol. 20, No. 23, Aug. 1, 2013, pp. 2929-2937, XP055268237.

Yu et al., "Fluorescent probes for hydrogen sulfide detection and bioimaging", Chemical Communications—ChemComm, vol. 50, No. 82, Jun. 6, 2014, pp. 12234-12249, XP055268282.

* cited by examiner

METHODS OF MEASURING HYDROGEN SULFIDE CONCENTRATIONS IN RESERVOIR FLUIDS

CROSS REFERENCE TO RELATED APPLICATONS

The present application is a National Stage (§ 371) application of PCT/US2016/020933, filed Mar. 4, 2016, which claims the benefit of U.S. Application No. 62/129,157, filed Mar. 6, 2015, which is incorporated herein by reference in its entirety.

BACKGROUND

The present disclosure relates generally to methods of measuring hydrogen sulfide concentrations in reservoir fluids. More specifically, in certain embodiments, the present disclosure relates to chemical probes useful for measuring hydrogen sulfide concentrations in reservoir fluids and associated methods and systems.

The presence of hydrogen sulfide is a common occurrence in a number of subsurface hydrocarbon reservoirs. The presence of hydrogen sulfide may be problematic, as it can be highly corrosive to casing, tubing, and other metallic and polymeric tools. Special care may need to be taken in recovering hydrocarbons from hydrogen sulfide containing reservoirs. As such, it is useful to determine the presence and concentration of hydrogen sulfide content of reservoir fluids before production begins.

Currently, the concentration of hydrogen sulfide in reservoir fluids is typically measured by analyzing samples captured using down hole fluid sampling tools. Two examples of downhole fluid sampling tools are the Modular Dynamics Tester from Schlumberger and the Reservoir Description Tool from Halliburton. These tools and methods of using them and other methods and tools are described in U.S. Pat. Nos. 6,223,822, 6,469,636, and 7,128,144, the entireties of which are hereby incorporated by reference.

Briefly, conventional downhole fluid sampling tools are lowered into a wellbore and used to collect reservoir fluid samples downhole in a sample container. The fluid from the sample container may then be transferred into smaller storage bottles which are shipped to a laboratory for hydrogen sulfide analysis using a sulfur chemiluminescence gas chromatography detector and/or a Draeger tube. One problem with these conventional methods it may take several weeks or months for the sample container or storage bottles to be transported to the lab and have the analysis completed. During that time, fluid present in the sample container or storage bottles may undergo drastic pressure and temperature changes. As a result of these changes and other factors, the hydrogen sulfide present in the sampling container or storage bottle may undergo irreversible transformations. Thus the amount of hydrogen sulfide measured in the laboratory may not accurately reflect the concentration of hydrogen sulfide present in the subterranean formation. Also, the presence of brine and oil phases in the sample may skew the hydrogen sulfide equilibrium in the sample thus further skewing the laboratory analysis of the sample. Furthermore, conventional storage bottles must be reheated and re-pressurized in the laboratory, however due to variation in the fill levels of storage bottles, the analysis of hydrogen sulfide may not accurately represent the reservoir fluid characteristics.

It is desirable to develop a method of measuring hydrogen sulfide concentrations in reservoir fluids that does not suffer from any of these conventional drawbacks.

SUMMARY

The present disclosure relates generally to methods of measuring hydrogen sulfide concentrations in reservoir fluids. More specifically, in certain embodiments, the present disclosure relates to chemical probes useful for measuring hydrogen sulfide concentrations in reservoir fluids and associated methods and systems.

In one embodiment the present disclosure provides a chemical probe composition comprising a base fluid and a chemical probe, wherein the chemical probe is capable of reacting with hydrogen sulfide to form a fluorophore.

In another embodiment, the present invention provides a method comprising: providing a chemical probe composition comprising a base fluid and a chemical probe, wherein the chemical probe is capable of reacting with hydrogen sulfide to form a fluorophore and introducing the chemical probe composition into a subterranean formation.

In another embodiment, the present invention provides a hydrogen sulfide measuring system comprising: a sampling device comprising chemical probe composition comprising a based fluid and a chemical probe, wherein the chemical probe is capable of reacting with hydrogen sulfide to form a fluorophore and a subterranean formation penetrated by a well bore, wherein the sampling device is located in the well bore.

BRIEF DESCRIPTION OF THE DRAWINGS

A more complete and thorough understanding of the present embodiments and advantages thereof may be acquired by referring to the following description taken in conjunction with the accompanying drawings.

The features and advantages of the present disclosure will be readily apparent to those skilled in the art. While numerous changes may be made by those skilled in the art, such changes are within the spirit of the disclosure.

DETAILED DESCRIPTION

The description that follows includes exemplary apparatuses, methods, techniques, and/or instruction sequences that embody techniques of the inventive subject matter. However, it is understood that the described embodiments may be practiced without these specific details.

The present disclosure relates generally to methods of measuring hydrogen sulfide concentrations in reservoir fluids. More specifically, in certain embodiments, the present disclosure relates to chemical probes useful for measuring hydrogen sulfide concentrations in reservoir fluids and associated methods and systems.

Some desirable attributes of the methods discussed herein are that they may allow for the more accurate measurement of hydrogen sulfide concentrations in reservoir fluids. Without wishing to be limited to theory, it is believed that the methods discussed herein may allow for the more accurate measurement of hydrogen sulfide concentration in reservoir fluids because they do not require the transportation of a sample fluid comprising the hydrogen sulfide to a lab for analysis. Rather, they allow the in-situ formation of a fluorophore and the subsequent measurement of the fluorophore concentration to determine the hydrogen sulfide concentration in the reservoir fluid. It is believed that this allows for the challenges associated with hydrogen sulfide losses caused by irreversible reaction, phase partitioning of hydrogen sulfide during transport, and reconstitution steps to be avoided due to the stability of the fluorophore.

In certain embodiments, the present disclosure provides a chemical probe composition. In certain embodiments, the chemical probe composition may comprise a base fluid and a chemical probe.

In certain embodiments, the base fluid may comprise an aromatic solvent. In certain embodiments, the aromatic solvent may be naphtha, diesel, kerosene, or a mixture thereof. In certain embodiments, the base fluid may be present in the chemical probe composition in an amount in the range of from 50 mol % to 99.9 mol %. In certain embodiments, the base fluid may be present in the chemical probe composition in an amount in the range of from 75 mol % to 99.9 mol %. In certain embodiments, the base fluid may be present in the chemical probe composition in an amount in the range of from 90 mol % to 99.9 mol %. In certain embodiments, the base fluid may be present in the chemical probe composition in an amount in the range of from 95 mol % to 99.9 mol %. In certain embodiments, the base fluid may be present in the chemical probe composition in an amount in the range of from 97.5 mol % to 99.9 mol %. In other embodiments, the base fluid may be present in the chemical probe composition in an amount in the range of from 95 mol % to 97.5 mol %. In other embodiments, the base fluid may be present in the chemical probe composition in an amount in the range of from 90 mol % to 95 mol %. In other embodiments, the base fluid may be present in the chemical probe composition in an amount in the range of from 75 mol % to 90 mol %.

In certain embodiments, the chemical probe may comprise any chemical probe that is capable of reacting with hydrogen sulfide in reservoir fluid and forming a stable compound that can be detected. As used herein, the term stable compound refers to a compound that is thermally stable in a crude oil system at temperatures up to 450° F. and capable of remaining dispersed or homogenously distributed in the crude oil system.

In certain embodiments, the chemical probe may comprise a chemical probe that is capable of selectively reacting with hydrogen sulfide in the presence of other sulfur containing compounds in-situ to form a fluorophore. As used herein, the term in-situ refers to the reaction occurring within a sample container or wellbore under wellbore conditions. In certain embodiments, the well bore conditions may be at temperatures in the range of from 50° F. to 450° F. and pressures in the range of from 1,000 to 30,000 psi.

In certain embodiments, the chemical probe may be a chemical probe that is capable of reacting with hydrogen sulfide to form a fluorophore by a nucleophilic cyclization reaction.

Figure 1:
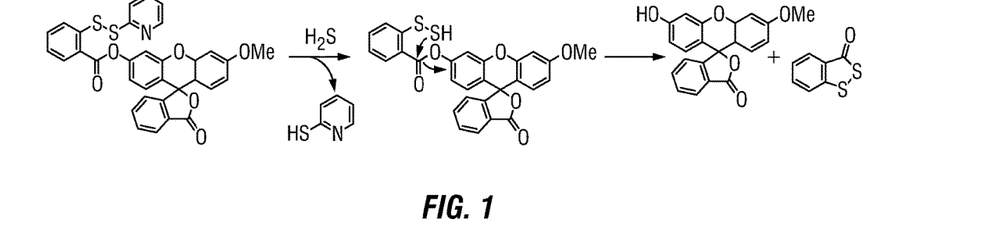
FIGS. 1-7 are illustrations of reaction mechanisms of several chemical probes.

In certain embodiments, the nucleophilic cyclization reaction may be a disulfide cleavage reaction of the chemical probe. Examples of suitable chemical probes that are capable of reacting with hydrogen sulfide to form a fluorophore by a disulfide cleavage reaction include "disulfide ester chemical probes." As used herein the term "disulfide ester chemical probe" refers to a chemical probe of the following structure:

wherein $R^1$ may be H, R (where R is a C2 to C20 alkyl group), OR' (where R' is H, a methyl group, or any ethyl group), R'OR" (where R' is C1 to C20 hydrocarbon chain and R" is H, a methyl group, an ethyl group, COMe, or COEt), or R'COOR" (where R' is a C1 to C20 hydrocarbon chain and R" is H, a methyl group, or an ethyl group). FIG. 1 illustrates a reaction mechanism of a disulfide ester chemical probe.

Figure 2:
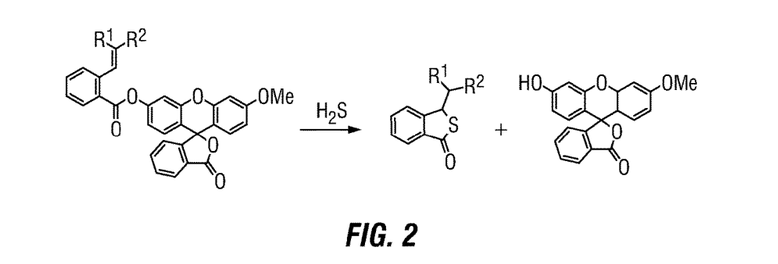

In certain embodiments the nucleophilic cyclization reaction may be an addition-cyclization reaction of the chemical probe. Examples of suitable chemical probes that are capable of reacting with hydrogen sulfide to form a fluorophore by an addition-cyclization reaction include "enone ester chemical probes." As used herein, the term "enone ester chemical probe" refers to a chemical probe of the following structure:

wherein $R^1$ may be $CO_2Me$, $CO_2Et$, or CN, $R^2$ may be $CO_2Me$, $CO_2Et$, or CN, and $R^3$ may be H, R (where R is a C1 to C20 alkyl group), OR' (where R' is H, a methyl group, or an ethyl group), R'OR" (where R' is a C1 to C20 hydrocarbon chain and R" is H, a methyl group, an ethyl group, a propyl group, COMe, COEt), R'''OH where R''' may be a methylene group, an ethylene group, or a propylene group), or R'COOR" (where R' is a C1 to C20 hydrocarbon chain and R" is H, a methyl group, or an ethyl group). FIG. 2 illustrates a reaction mechanism of an enone ester chemical probe.

Figure 3:
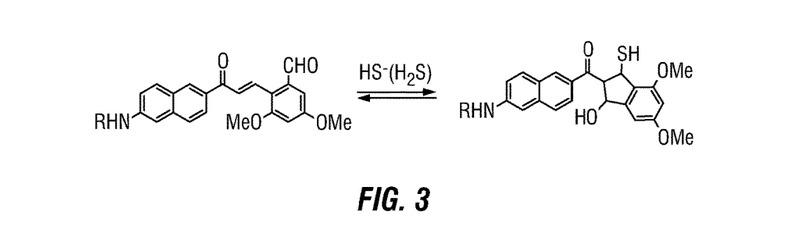

In certain embodiments, the nucleophilic cyclization reaction may be a Michael addition & aldol condensation reaction. Examples of suitable chemical probes that are capable of reacting with hydrogen sulfide to form a fluorophore by a Michael addition & aldol condensation reaction include "aldehyde-enoate or aldehyde-enone chemical probes." As used herein, the term "aldehyde-enoate or aldehyde-enone chemical probes" refers to a chemical probe of the following structure:

wherein $R^1$, $R^2$ and $R^3$ may each be independently one of the following: H, R (where R is a C1 to C20 alkyl group), OR' (where R' is H, a methyl group, or an ethyl group), R'OR" (where R' is a C1 to C20 hydrocarbon chain and R" is H, a methyl group, an ethyl group, a propyl group, COMe, COEt), R'''OH (where R''' is a methylene group, an ethylene group, or a propylene group), or R'COOR" (where R' is a C1 to C20 hydrocarbon chain and R" is H, a methyl group, or an ethyl group). FIG. 3 illustrates a reaction mechanism of an aldehyde-enoate or aldehyde-enone chemical probe.

In certain embodiments, the chemical probe may be a chemical probe that is capable of reacting with hydrogen sulfide to form a fluorophore by a chemical reduction reaction.

Figure 4:
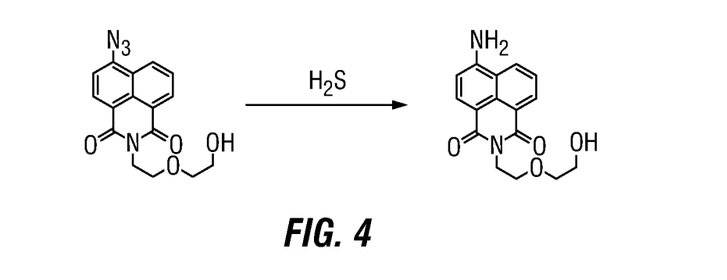

In certain embodiments, the chemical reduction reaction may be a chemical reduction of a $N_3$ group to $NH_2$ on a chemical probe. Examples of suitable chemical probes that are capable of undergoing a $N_3$ group reduction to form a fluorophore include "aryl azide or aryl sulfonyl azide chemical probes." As used herein, the term "aryl azide or aryl sulfonyl azide chemical probe" refers to any chemical probe with any of the following structures:

wherein $R^1$ and $R^2$ may each independently be H, R (where R is a C1 to C20 alkyl group), OR' (where R' is H, a methyl group, or an ethyl group), R'OR" (where R' is a C1 to C20 hydrocarbon chain and R" is H, a methyl group, an ethyl group, a propyl group, COMe, COEt), R'''OH (where R''' is a methylene group, an ethylene group, or a propylene group), or R'COOR" (where R' is a C1 to C20 hydrocarbon chain and R" is H, a methyl group, or an ethyl group). FIG. 4 illustrates a reaction mechanism of an aryl azide or aryl sulfonyl azide chemical probe.

Figure 5:
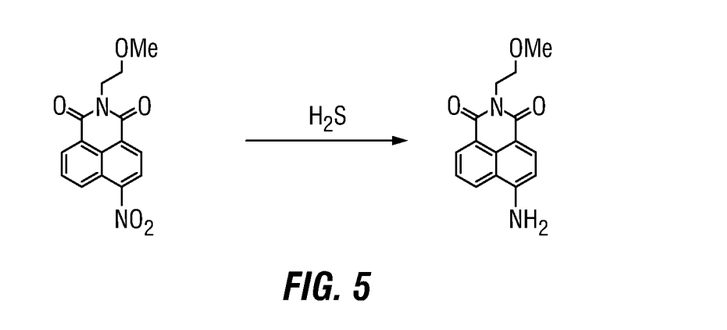

In certain embodiments, the chemical reduction reaction may be a chemical reduction of a $NO_2$ group to $NH_2$ on a chemical probe. Examples of suitable chemical probes that are capable of undergoing an $NO_2$ group reduction to form a fluorophore include "4-nitro naphthalimide derivate chemical probes." As used herein, the term "4-nitro naphthalimide derivate chemical probe" refers to a chemical probe of the following structure:

wherein $R_1$ may be H, R (where R is a C1 to C20 alkyl group), R'OR" (where R' is a C1 to C20 hydrocarbon chain and R" is H, a methyl group, an ethyl group, a propyl group, COMe, COEt, R'''OH (where R''' is a methylene group, an ethylene group, or a propylene group), or R'COOR" (where R' is a C1 to C20 hydrocarbon chain and R" is H, a methyl group, or an ethyl group). FIG. 5 illustrates a reaction mechanism of a 4-nitro naphthalimide derivate probe.

Figure 6:
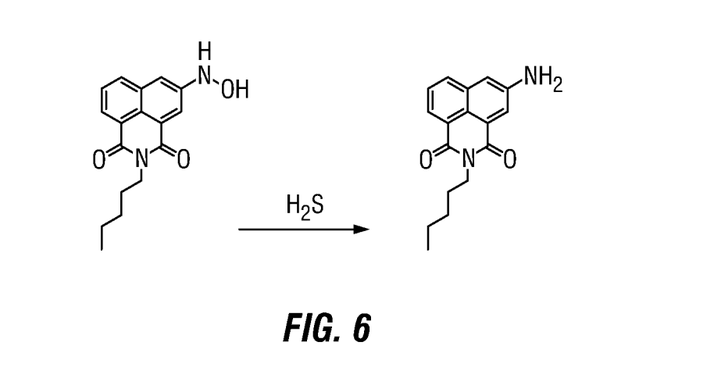

In certain embodiments, the chemical reduction reaction may be a chemical reduction of a HNOH group to $NH_2$. Examples of suitable chemical probes that are capable of undergoing an HNOH group reduction to form a fluorophore include "5-hydroxyamino napthtalimide chemical probes." As used herein, the term "5-hydroxyamino naphthalimide chemical probe" refers to a chemical probe of the following structure:

wherein $R_1$ may be H, R (where R is a C1 to C20 hydrocarbon chain), R'OR" (where R' is a C1 to C20 hydrocarbon chain and R" is H, a methyl group, an ethyl group, a propyl group, COMe, COEt), R'"OH (where R'" is a methylene group, an ethylene group, or a propylene group), or R'COOR" (where R' is a C1 to C20 hydrocarbon chain and R" is H, a methyl group, or an ethyl group). FIG. 6 illustrates a reaction mechanism of a 5-hydroxyamino napththalimide chemical probe.

Figure 7:
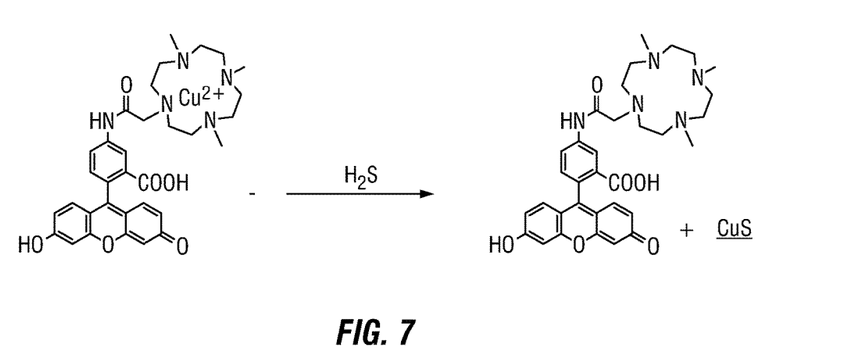

In certain embodiments, the chemical probe may be a chemical probe that is capable of reacting with hydrogen sulfide to form a fluorophore by a metal sulfide formation reaction. Examples of suitable chemical probes that are capable of reacting with hydrogen sulfide to form a fluorophore by a metal sulfide formation reaction include "azamacrocylic copper (II) ion complex chemical probes." As used herein, the term "azamacrocylic copper (II) ion complex chemical probe" refers to a chemical probe of any of the following structures:

wherein R has one of the following structures:

FIG. 7 illustrates a reaction mechanism of an azamacrocylic copper (II) ion complex probe.

In certain embodiments, the fluorophore formed by the reaction of the chemical probe and the hydrogen sulfide may be detected by fluorescence spectroscopy (spectrometer), to obtain quantitative information on the hydrogen sulfide content in the reservoir fluid. In certain embodiments, the fluorophore formed may remain stable in the reservoir fluid in the sample cylinder and taken to a lab for analysis of the fluorescence emission intensity of the fluid. The measured fluorescence emission intensity of the fluid may then be compared to known standards to determine the hydrogen sulfide concentration in the reservoir fluid.

In certain embodiments, the amount of chemical probe present in the chemical probe composition may be enough to test an hydrogen sulfide concentration in the reservoir fluid as low as 0.1 mg/L or as high as 5 mol %. In certain embodiments, the amount of chemical probe present in the chemical probe composition may be an amount in the range of from 0.1 mol % to 50 mol %. In certain embodiments, the amount of chemical probe present in the chemical probe composition may be an amount in the range of from 0.1 mol % to 25 mol %. In certain embodiments, the amount of chemical probe present in the chemical probe composition may be an amount in the range of from 0.1 mol % to 10 mol %. In certain embodiments, the amount of chemical probe present in the chemical probe composition may be an amount in the range of from 0.1 mol % to 5 mol %. In certain embodiments, the amount of chemical probe present in the chemical probe composition may be an amount in the range of from 0.1 mol % to 2.5 mol %. In other embodiments, the amount of chemical probe present in the chemical probe composition may be an amount in the range of from 2.5 mol % to 5 mol %. In other embodiments, the amount of chemical probe present in the chemical probe composition may be an amount in the range of from 5 mol % to 10 mol %. In other embodiments, the amount of chemical probe present in the chemical probe composition may be an amount in the range of from 10 mol % to 25 mol %.

In certain embodiments, the present disclosure provides a method comprising: providing a chemical probe composition and introducing the chemical probe composition into a subterranean formation.

In certain embodiments, the chemical probe that is introduced into the subterranean formation may comprise any chemical probe composition discussed above. In certain embodiments, the subterranean formation may comprise a subterranean formation that is penetrated by a well bore.

In certain embodiments, introducing the chemical probe composition into the subterranean formation may comprise placing the chemical probe composition into a sample container and lowering the sample container into a wellbore penetrating the subterranean formation. In certain embodiments, the sample container may comprise any conventional sample container. Examples of conventional sample containers include floating piston sampling cylinders such as the MPSR (multisample production sample receptacle) or SPMC (single phase multi-sample chamber) sampling bottles commercially available from Schlumberger.

In certain embodiments, the amount of chemical probe composition placed into the sample container may be an amount in the range of from 0.1 cc to 5 cc. In certain embodiments, the amount of chemical probe composition placed in the sample container may be an amount equal to 0.1% to 1% of the volume of the sample container. In certain embodiments, the amount of chemical probe composition placed in the sample container may be an amount sufficient to measure concentrations of hydrogen sulfide in the reservoir fluid collected in the sample container in the range of from 1 ppm to 100 ppm. In certain embodiments, lowering the sample container into the wellbore penetrating the subterranean formation may comprise lowering the sample container into the well bore using a modular dynamic formation tester. In certain embodiments, the sample container may be lowered into reservoir fluid present in the wellbore.

In certain embodiments, the method may further comprise collecting a sample of the reservoir fluid. In certain embodiments, collecting a sample of the reservoir fluid may comprise allowing reservoir fluid to enter into the sample container. In certain embodiments, the amount of reservoir fluid collected in the sample container may be an amount in the range of from 10 cc to 20,000 cc. In certain embodiments, the amount of reservoir fluid collected in the sample container may be an amount equal to 20% to 99% of the volume of the sample container. In certain embodiments, the amount of reservoir fluid collected in the sample container may be an amount sufficient to ensure the ratio of hydrogen sulfide to chemical probe in the sample container is greater than 1.

In certain embodiments, the method may further comprise allowing any hydrogen sulfide present in the sample of reservoir fluid collected to react with the chemical probe in the chemical probe composition. In certain embodiments, allowing the hydrogen sulfide present in the sample of reservoir fluid collected to react with the chemical probe in the chemical probe composition may further comprise forming a fluorophore. In certain embodiments, the amount of fluorophore formed may be directly proportional to the amount of hydrogen sulfide present in the reservoir fluid.

In certain embodiments, all of the hydrogen sulfide present in the sample of reservoir fluid may react with the chemical probe to form a fluorophore. In other embodiments, 95 to 99.9% of the hydrogen sulfide present in the sample of the reservoir fluid may react with the chemical probe to form a fluorophore.

In certain embodiments, the method may further comprise raising the sample container to the surface. In certain embodiments, a modular dynamic formation tester may be used to raise the sample container to the surface.

In certain embodiments, the method may further comprise analyzing the reservoir fluid to determine the amount of fluorophore present in the sample container. In certain embodiments, analyzing the collected fluid sample to determine the amount of fluorophore present in the sample container may first comprise using a fluorescence spectrometer to determine the amount of fluorophore. In certain embodiments, using a fluorescence spectrometer may first comprise using an external fluorophore standard to generate a calibration curve of fluorescence emission intensity as a function of fluorophore standard concentration which will be proportional to hydrogen sulfide concentration on mole basis. In certain embodiments, the measured fluorescence emission intensity from the reservoir fluid may be plotted against the calibrated emission curve to determine hydrogen sulfide content in the reservoir fluid. In certain embodiments, the method may further comprise cooling the sample container before analysis. In certain embodiments, the reservoir fluid in the sample container may be analyzed at room temperature near atmospheric pressure.

In certain embodiments, the present disclosure provides a method comprising: providing a chemical probe composition, introducing the chemical probe composition into a subterranean formation comprising hydrogen sulfide, and allowing the chemical probe composition to react with the hydrogen sulfide to form a fluorophore.

In certain embodiment, the chemical probe composition may comprise any chemical probe composition discussed above. In certain embodiments, the subterranean formation may comprise any subterranean formation discussed above. In certain embodiments, the fluorophore may comprise any fluorophore discussed above.

Figure 8:
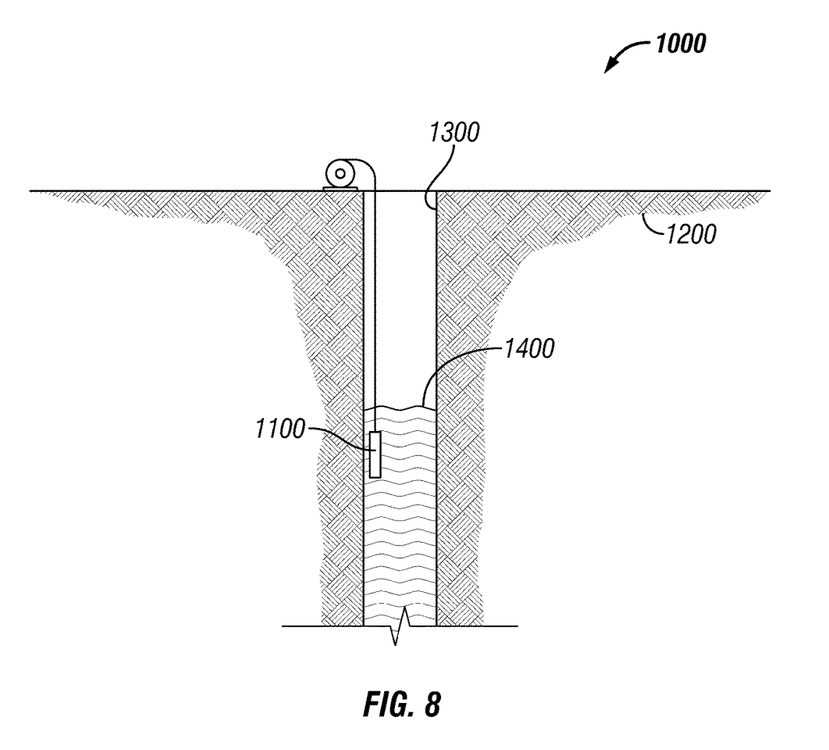
FIG. 8 is an illustration of a hydrogen sulfide measurement system in accordance with certain embodiments of the present disclosure.

Referring now to FIG. 8, FIG. 8 illustrates a hydrogen sulfide sampling system 1000. In certain embodiments, hydrogen sulfide sampling system 1000 may comprise a sampling device 1100, a subterranean formation 1200, and well bore 1300. In certain embodiments, a reservoir fluid 1400 comprising hydrogen sulfide may be present within well bore 1300. In certain embodiments, sampling device 1100 may be present in the reservoir fluid 1400.

In certain embodiments, sampling device 1100 may comprise any sample container discussed above. In certain embodiments, a chemical probe composition may be placed within sampling device 1100. In certain embodiments, subterranean formation 1200 may comprise any subterranean formation discussed above. In certain embodiments, well bore 1300 may comprise any wellbore discussed above. In certain embodiments, reservoir fluid 1400 may comprise any reservoir fluid discussed above. In certain embodiments, a portion of reservoir fluid 1400 may flow into sampling device 1100.

While the embodiments are described with reference to various implementations and exploitations, it will be understood that these embodiments are illustrative and that the scope of the inventive subject matter is not limited to them. Many variations, modifications, additions and improvements are possible.

Plural instances may be provided for components, operations or structures described herein as a single instance. In general, structures and functionality presented as separate components in the exemplary configurations may be implemented as a combined structure or component. Similarly, structures and functionality presented as a single component may be implemented as separate components. These and other variations, modifications, additions, and improvements may fall within the scope of the inventive subject matter.

That which is claimed is:

1. A chemical probe composition comprising a base fluid and a chemical probe, wherein the chemical probe is configured to react with hydrogen sulfide in a reservoir fluid to form a fluorophore, wherein the chemical probe is selected from the group consisting of disulfide ester chemical probes, enone ester chemical probes, aldehvde-enoate chemical probes, aldehyde enone chemical probes, aryl azide chemical probes, aryl sulfonyl azide chemical probes, 4-nitro naphthalimide derivate chemical probes, 5-hydroxyamlno napthlhalimide chemical probes, azamacrocylic copper (II) ion complex chemical probes and combinations thereof.

2. The chemical probe composition of claim 1, wherein the base fluid comprises an aromatic solvent.

3. The chemical probe composition of claim 1, wherein the chemical probe is capable of reacting with hydrogen sulfide to form a fluorophore by a nucleophilic cyclization reaction.

4. The chemical probe composition of claim 3, wherein the nucleophilic cyclization reaction is a disulfide cleavage reaction of the chemical probe.

5. The chemical probe composition of claim 3, wherein the nucleophilic cyclization reaction is an addition-cyclization reaction of the chemical probe.

6. The chemical probe composition of claim 3, wherein the nucleophilic cyclization reaction is a Michael addition & aldol condensation reaction.

7. The chemical probe composition of claim 1, wherein the chemical probe is capable of reacting with hydrogen sulfide to form a fluorophore by a chemical reduction reaction.

8. The chemical probe composition of claim 7, wherein the chemical reduction reaction is a $N_3$ group reduction reaction.

9. The chemical probe composition of claim 7, wherein the chemical reduction reaction is an $NO_2$ group reduction reaction.

10. The chemical probe composition of claim 7, wherein the chemical reduction reaction is an HNOH group reduction reaction.

11. The chemical probe composition of claim 1, wherein the chemical probe is capable of reacting with hydrogen sulfide to form a fluorophore by a metal sulfide formation reaction.

12. The chemical probe composition of claim 1, wherein the chemical probe is present in the chemical probe composition in an amount in the range of from 0.1 mol % to 5 mol %.

13. The chemical probe composition of claim 1, wherein the base fluid is present in the chemical probe composition in an amount in the range of from 95 mol % to 99.9 mol %.

14. A method comprising: providing a chemical probe composition comprising a base fluid and a chemical probe, wherein the chemical probe reacts with hydrogen sulfide in a reservoir fluid to form a fluorophore, wherein the chemical probe is selected from the group consisting of disulfide ester chemical probes, enone ester chemical probes, aldehvde-enoate chemical probes, aldehyde enone chemical probes, aryl azide chemical probes, aryl sulfonyl azide chemical probes, 4-nitro naphthalimide derivate chemical probes, 5-hydroxyamlno napthlhalimide chemical probes, azamacrocylic copper (II) ion complex chemical probes and combinations thereof, and introducing the chemical probe composition into a subterranean formation.

15. The method of claim 14, wherein the chemical probe composition comprises the chemical probe composition of any one of claims 2-13.

16. The method of claim 14, wherein introducing the chemical probe composition into the subterranean formation comprises placing the chemical probe composition into a sample container and lowering the sample container into a wellbore penetrating the subterranean formation.

17. The method of claim 16, further comprising allowing a portion of the reservoir fluid to enter into sample container.

18. The method of claim 14, further comprising allowing the chemical probe to react with hydrogen sulfide to form a fluorophore.

19. The method of claim 18, further comprising measuring the concentration of the fluorophore.

20. A hydrogen sulfide measuring system comprising:
a sampling device comprising a chemical probe composition comprising a base fluid and a chemical probe, wherein the chemical probe is configured to react with hydrogen sulfide in a reservoir fluid to form a fluorophore, wherein the chemical probe is selected from the group consisting of disulfide ester chemical probes, enone ester chemical probes, aldehvde-enoate chemical probes, aldehyde enone chemical probes, aryl azide chemical probes, aryl sulfonyl azide chemical probes, 4-nitro naphthalimide derivate chemical probes, 5-hydroxyamlno napthlhalimide chemical probes, azamacrocylic copper (II) ion complex chemical probes and combinations thereof, and a subterranean formation penetrated by a well bore, wherein the sampling device is located in the well bore.

* * * * *